United States Patent [19]

Scholz

[11] Patent Number: 5,285,999
[45] Date of Patent: Feb. 15, 1994

[54] LOW PRESSURE VALVE HAVING TWO RELATIVELY ROTATABLE SECTIONS

[76] Inventor: Michael P. Scholz, 118 Vua Zapata, San Clemente, Calif. 92672

[21] Appl. No.: 27,330

[22] Filed: Mar. 5, 1993

[51] Int. Cl.⁵ .......................................... F16K 31/528
[52] U.S. Cl. ..................... 251/252; 251/346
[58] Field of Search ............... 251/252, 253, 254, 351, 251/346, 343; 222/520, 521

[56] References Cited

U.S. PATENT DOCUMENTS

| | | | |
|---|---|---|---|
| 1,904,739 | 4/1933 | Kroen | 222/521 |
| 2,797,888 | 7/1957 | Sachs | 251/252 |
| 3,351,249 | 11/1967 | Stull | 222/520 |
| 4,810,471 | 3/1989 | Wachob | 422/103 |

FOREIGN PATENT DOCUMENTS 686  2/1979  European Pat. Off. ............ 222/521

Primary Examiner—Robert G. Nilson
Attorney, Agent, or Firm—Burns, Doane, Swecker & Mathis

[57] ABSTRACT

A valve comprises upper and lower sections which are rotatable relative to one another about a longitudinal axis. Relative rotation in one direction causes the valve to open, and relative rotation in the opposite direction causes the valve to close. Opening and closing of the valve is caused by a camming arrangement between the two valve sections. One of the valve sections includes an outer skirt which is cammed outwardly as the valve sections are axially forced together during assembly, to enable the cam elements to snap together. Each valve section is of one piece plastic molded construction.

14 Claims, 3 Drawing Sheets

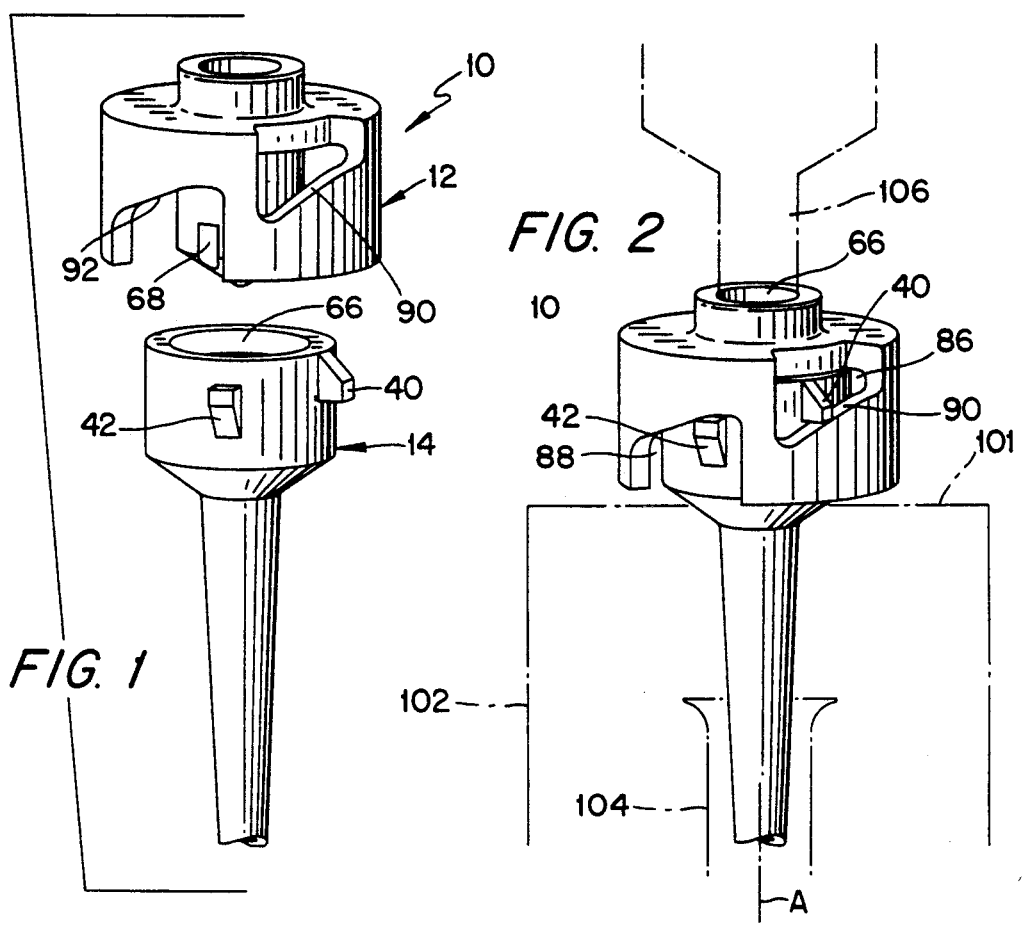
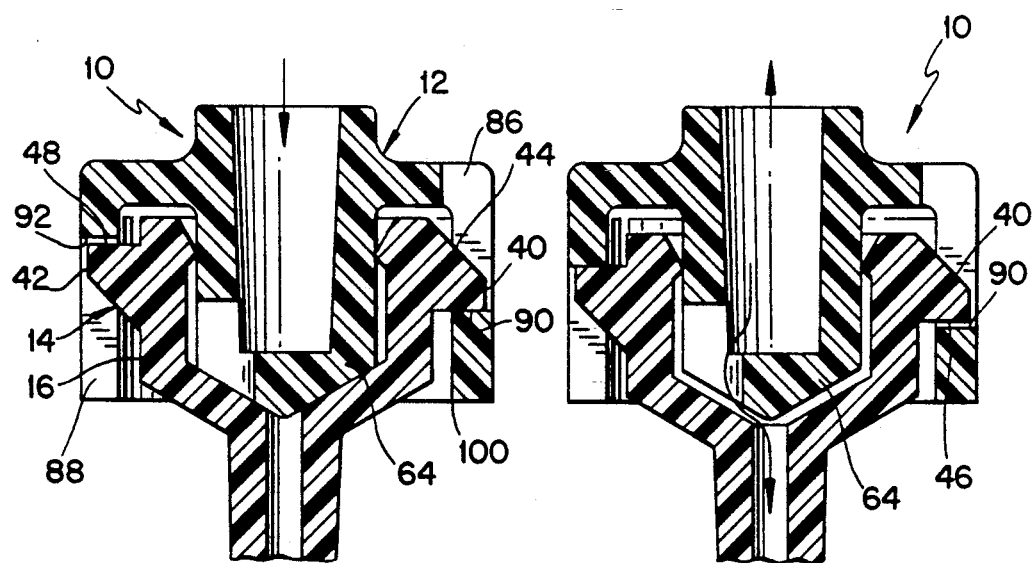
FIG. 1
FIG. 2
FIG. 3
FIG. 4

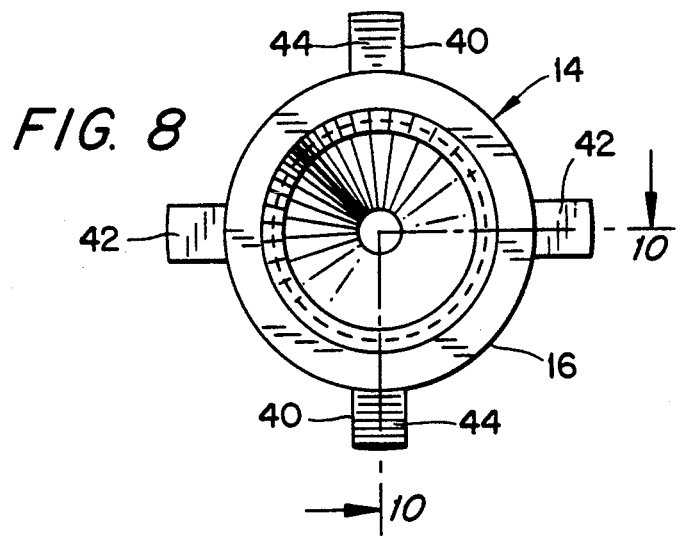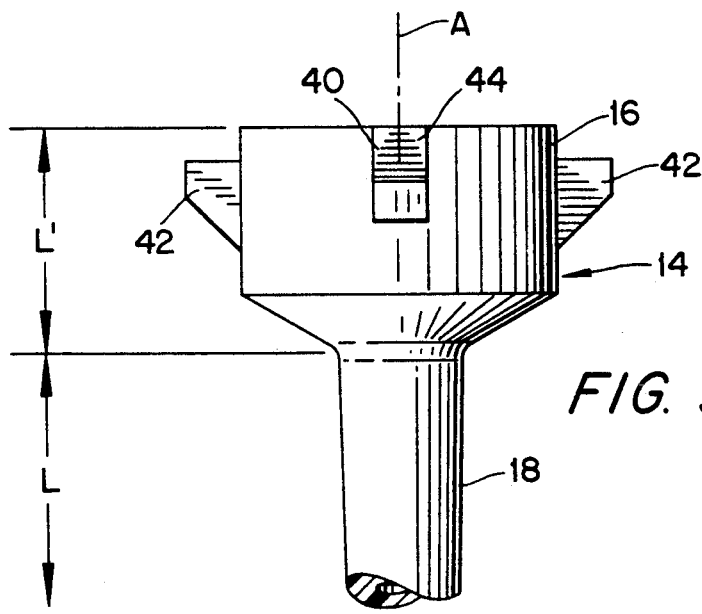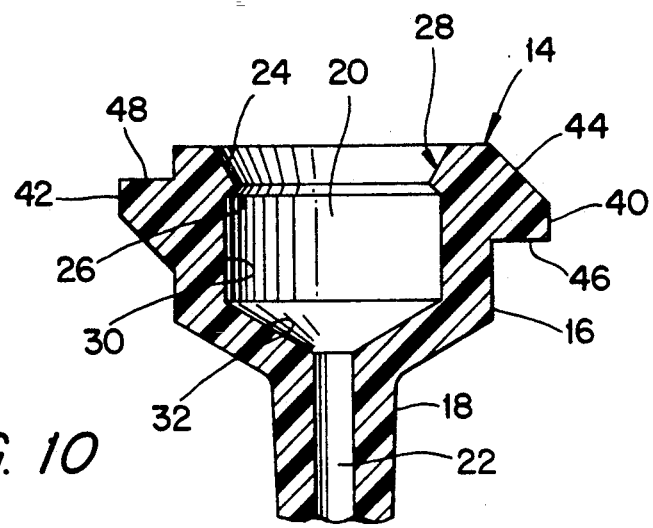

5,285,999

LOW PRESSURE VALVE HAVING TWO RELATIVELY ROTATABLE SECTIONS

BACKGROUND OF THE INVENTION

The present invention relates to valves, especially to valves used in connection with a vacuum manifold device for treating liquid samples.

Liquid samples may be treated to test for and/or remove the same or different constituents in the samples, e.g. by solid phase extraction or filtering. In carrying out the treatment, one proposed system, disclosed in U.S. Pat. No. 4,810,471, includes a reagent tube mounted atop a valve and connected to a valve inlet. A long tube connects the valve outlet with a vacuum manifold device disposed therebelow. The sample is introduced into an upper end of the reagent tube, and the valve is opened. Then, a vacuum is applied to the vacuum manifold device to draw the sample through the reagent tube, the valve and the long tube and delivered to a collection container disposed in the vacuum manifold device.

The valve is a low pressure valve comprised of members which are threadedly interconnected such that rotation of one member causes the valve to open or close. The threaded members are formed of plastic, and probably should be machined in order to obtain the necessary dimensional precision.

It would be desirable to provide valve members that can be made by a molding step without any appreciable machining.

Also, it would be desirable to minimize the number of components of the valve. In the above-described U.S. Pat. No. 4,810,471 the valve comprises two threadedly connected parts, a valve seat part disposed between those parts to define a valve seat, and the long tube which is mounted on one of the valve parts.

SUMMARY OF THE INVENTION

The present invention relates to a valve comprising first and second plastic valve sections each being of one piece molded construction. The first valve section comprises a head forming a chamber which defines a longitudinal axis. One axial end of the chamber is open in a first axial direction. A first fluid passage is disposed at a second axial end of the chamber. A plurality of circumferentially spaced first cam faces is disposed on an outer periphery of the head. The first cam faces are arranged to face in a second axial direction which is opposite the first axial direction. A plurality of circumferentially spaced second cam faces is disposed on the outer periphery of the head. The second cam faces are arranged to face in the first axial direction. The second valve section comprises an end wall, and a closure extending from the end wall in the second axial direction and disposed in the chamber. The closure includes a passage-closing end which faces the first passage for opening and closing that passage in response to axial movement of the second section in first and second axial directions, respectively. A second fluid passage extends through the end wall and closure and communicates with the chamber at a location spaced axially from the passage-closing end of the closure. A skirt extends from the end wall in the second axial direction and extends axially around the closure. The skirt is spaced radially outwardly from the closure to form a space therebetween in which the head is disposed. A plurality of circumferentially spaced first cam follower faces is disposed on the skirt. The first cam follower faces are engageable with respective first cam faces of the first section and are responsive to relative rotation between the first and second valve sections in a first rotary direction to produce movement of the first valve section in the second axial direction for closing the valve. A plurality of circumferentially spaced second cam follower faces is disposed on the skirt. The second cam follower faces are engageable with respective second cam faces of the first section and are responsive to the relative rotation in a second rotary direction opposite the first rotary direction to produce movement of the first section in the second axial direction for opening the valve.

Preferably, an annular lip is formed between the chamber and closure for producing a friction fit between the first and second valve sections.

Preferably, one of the first and second valve sections includes camming faces which cam the skirt radially outwardly as the first and second valve sections are pushed axially together, in order to enable the cam follower faces to engage the cam faces.

Preferably, the first valve section includes an axially projecting stem which forms the first fluid passage. The stem has a length at least five times as great as a length of the head.

BRIEF DESCRIPTION OF THE DRAWING

The objects and advantages of the invention will become apparent from the following detailed description of preferred embodiments thereof in connection with the accompanying drawing in which like numerals designate like elements and in which:

FIG. 1 is an exploded perspective view of a valve according to the present invention;

FIG. 2 is a view similar to FIG. 1 with the valve sections shown in an assembled condition, and mounted in a vacuum manifold arrangement shown in phantom lines;

FIG. 3 is a longitudinal sectional view taken through the valve depicted in FIG. 2, when the valve is in a closed state;

FIG. 4 is a view similar to FIG. 3 with the valve in an open state;

FIG. 8 is a top end view of a lower section of the valve;

FIG. 9 is a side elevational view of the lower valve section; and

FIG. 10 is a sectional view taken along the line 10—10 in FIG. 8.

DETAILED DESCRIPTION OF A PREFERRED EMBODIMENT OF THE INVENTION

Figure 5:
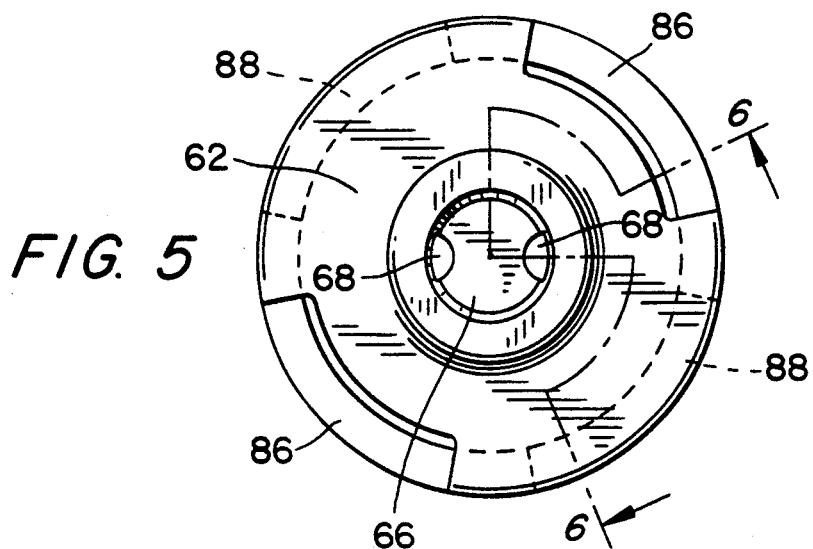
FIG. 5 is a view of a top end of an upper valve section of the valve.

A valve 10 comprises upper and lower relatively rotatable sections 12, 14. Each of the valve sections 12, 14 is of one-piece, plastic, molded construction. The lower section 14, depicted in detail in FIGS. 8-10, comprises an enlarged upper head 16 and a hollow elongated lower stem 18. The head 16 is of generally cylindrical shape and forms a longitudinal axis A which passes centrally through the stem 18. The stem 18 has a length L which is many times (e.g., five times) as long as the length L' of the head 16. Disposed in the head 16 is a chamber 20 (see FIG. 10) which is open in an upper axial direction and communicates at its lower axial end with an internal passage 22 formed by the stem 18.

The chamber 20 includes a frusto-conical first portion 24 which narrows downwardly, and a frusto-conical second portion 26 disposed below the first portion 24 and narrowing upwardly. The second portion 26 intersects the first portion 24 to define a radially inwardly projecting lip 28.

The chamber 20 further comprises a cylindrical third portion 30 disposed below the section, and a frusto-conical fourth portion 32 disposed below the third portion 30. That fourth portion 32 narrows downwardly and intersects the stem passage 22.

Projecting radially outwardly from an outer peripheral surface of the head 16 are two pairs of cam elements 40, 42. A first pair 40 of the cam elements are diametrically opposed, and are offset by 90 degrees relative to the cam elements of the second pair 42. Each cam element 40 of the first pair includes an inclined cam face 44 which extends downwardly and outwardly from the top of the head 16, and a downwardly facing cam 46 which lies generally in a radial plane, although other configurations of the cam face 46 are possible.

Each cam element 42 of the second pair includes an upwardly facing cam face 48 which lies in a radial plane. Other configurations of the cam face 48 are possible. The cam face 48 is spaced below the top of the head 16.

Figure 6:
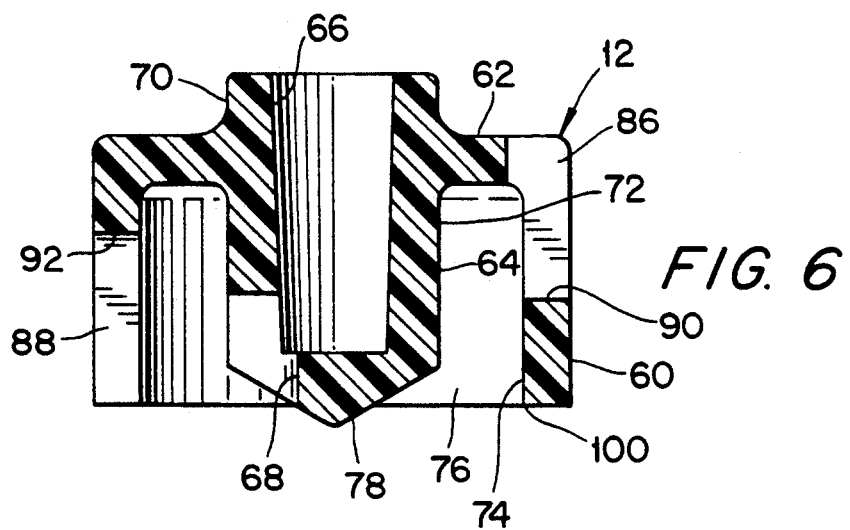
FIG. 6 is a sectional view taken along the line 6—6 in FIG. 5.
Figure 7:
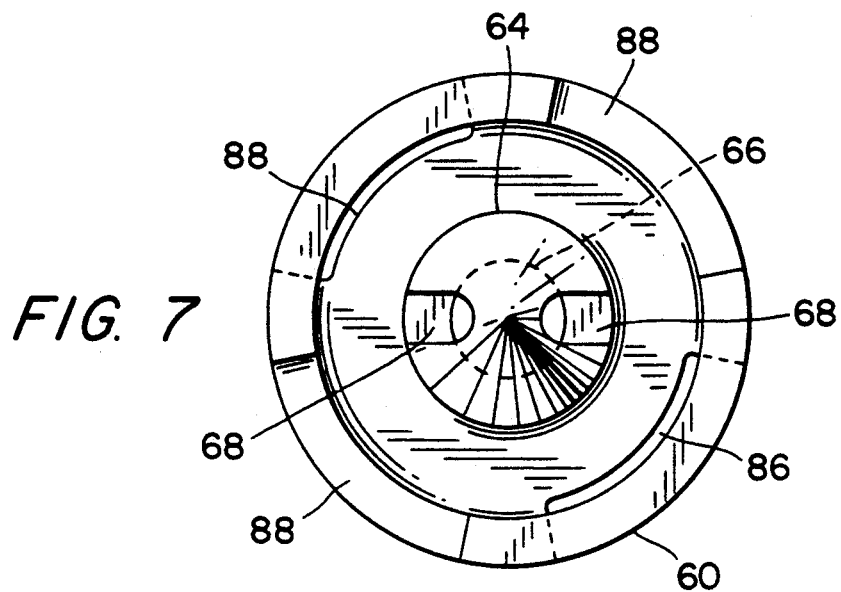
FIG. 7 is a bottom end view of the upper valve section.

The upper valve section 12, best illustrated in FIGS. 5–7, comprises a cylindrical outer skirt 60 projecting downwardly from the outer periphery of a top end wall 62, and a closure 64 projecting downwardly from the center of the top end wall 62. A passage 66 extends downwardly through the center of both the top end wall 62 and the closure 64 and communicates with a pair of diametrically opposite holes 68 formed adjacent a lower end of the closure 64. (Only one hole 68 is depicted in FIG. 6, due to the nature of the section plane 6—6 in FIG. 5.) An upper end of the passage 66 is formed as an upwardly projecting hub 70 of the top end wall 62.

A cylindrical outer peripheral surface 72 of the closure 64 is of smaller diameter than a cylindrical inner surface 74 of the skirt 60 to form therebetween an annular space 76 which receives the head 16 of the lower valve section 14. The closure 64 also includes a downwardly narrowing frusto-conical nose 78 which is adapted to close the passage 22 of the stem 18 as also will be later explained. Each of the holes 68 is located axially above the nose 78 so that the nose 78 is able to close the stem passage 22 when pressed against the surface 32 of the chamber 20.

Formed in the skirt 60 are recesses defined by two pairs of apertures 86, 88. The apertures 86 of the first pair are diametrically opposed, and the apertures 88 of the second pair are also diametrically opposed and are offset by 90 degrees relative to the apertures 86. Each aperture 88 extends all the way to the lower end of the skirt 60.

Each aperture 86 includes an upwardly facing cam follower face 90 (see FIG. 1) against which a cam element 40 may ride during valve operation. Likewise, each aperture 88 includes a downwardly facing cam follower face 92 against which the cam element 42 may ride during valve operation. In particular, the cam face 46 of each cam element 40 is engageable with a respective cam follower face 90, and the cam face 48 of each cam element 42 is engageable with a respective cam follower face 92. The cam follower faces 90, 92 are configured so that: (a) when the upper valve section 12 is rotated in one direction relative to the lower valve section 14, the cam follower faces 90 are pushed axially downwardly by the cam faces 46, (see FIG. 3), and (b) when the upper valve section 12 is rotated in the opposite direction, the cam follower faces 92 are pushed axially upwardly by the cam faces 48 (see FIG. 4).

When the cam follower faces 90 are pushed axially downwardly, the valve closes. That is, the nose 78 of the closure 64 engages the surface 32 of the chamber 20 to close the stem passage 22 (see FIG. 3). Conversely, when the cam follower faces 92 are pushed axially upwardly, the valve opens. That is, the closure 64 is raised to communicate the stem passage 22 with the passage 66, 68 formed in the upper valve section 12 (see FIG. 4). It will be appreciated that the extent of rotation of the upper valve section 12 is limited by contact of the cam elements 40, 42 with the walls of their respective apertures 86, 88. At the extreme positions of rotation of the upper valve section 12, the valve will be fully open or closed; at all intermediate positions, the valve will be partially open by varying amounts.

To assemble the valve 10, the upper section 12 is pushed axially downwardly onto the head 16, with the apertures 88 being axially aligned with the cam elements 42. In so doing, a lower edge 100 of the skirt 60 will engage the cam faces 44 of the cam elements 40, whereupon the lower end of the skirt is flexed radially outwardly to pass over the cam elements 40. When the cam elements 40 become radially aligned with the apertures 86, the skirt will snap back to lock the upper section 12 against axial removal from the lower section 14. The diameter of the outer surface 72 of the closure 64 is slightly greater than the inner diameter of the lip 28 of the lower valve section 14, so that a friction fit is formed therebetween to hold the valve in its various positions of adjustment. Also, the friction fit will produce a fluid seal which is ample in the case of low pressure valves of the presently disclosed type.

In use, the valve 10 is assembled as explained above, and the lower section 14 of the valve is mounted non-rotatably in the cover 101 of a vacuum manifold device 102 such that the stem 18 extends into a collection tube 104 disposed within the device 102. A luer-type fitting of a reagent tube 106, such as a solid phase extraction (SPE) column or filtration device, is inserted into the passage 66 of the upper valve section 12, and a liquid sample is introduced into the upper end of the reagent tube 106. Although only one reagent tube 106 is shown, in practice many reagent tubes would be used and would be connected to respective valves 10.

Then, the valve 10 is opened by rotating the reagent tube 106 in a valve-opening direction about the axis A. This, in turn, causes the upper section 12 of the valve to rotate and rise as the cam follower faces 92 ride along the cam faces 48, thereby lifting the closure 64 to open the passage 22. Then, a vacuum is applied within the vacuum manifold device 102 to draw the liquid through the reagent tube 106 and the valve 10 and into the collection tube 104 in the usual manner. When it becomes necessary to block the vacuum from the reagent tube 106, e.g. when refilling the reagent tube, the reagent tube is rotated in a valve-closing direction about the axis A. In so doing, the upper valve section 12 is rotated to bring the cam follower face 90 into engagement with the cam face 46 to push the upper valve portion 12 downwardly. This causes the nose 78 of the closure 64 to close the stem passage 22.

It will be appreciated that the present invention provides a highly simplified, fast acting valve arrangement which comprises only two plastic pieces 12, 14. This eliminates the need for an expensive machining step as would be required to produce threadedly coupled valve sections.

Also, the lower valve section 14 includes an integral long stem which extends deeply into the collection valve for minimizing spatter and atomizing of the liquid. This eliminates the need for attaching a separate long tube to the valve.

It will be appreciated that the apertures 86, 88 formed in the skirt 60 need not extend completely radially through the skirt in order to form recesses for receiving the cam elements 40, 42. Also, the lower end of the skirt 60 could be bevelled to eliminate the need for the cam faces 44.

The valve 10 according to the present invention could be used in systems other than that disclosed herein, e.g., in non-vacuum systems.

Although the present invention has been described in connection with preferred embodiments thereof, it will be appreciated by those skilled in the art that additions, deletions, modifications, and substitutions are specifically described and may be made without departing from the spirit and scope of the invention as defined in the appended claims.

What is claimed is:

1. A valve comprising first and second plastic valve sections each being of one-piece molded construction, said first valve section comprising:
    a head forming a chamber which defines a longitudinal axis, one axial end of said chamber being open in a first axial direction, and a first fluid passage being disposed at a second axial end of said chamber,
    a plurality of circumferentially spaced first cam faces disposed on an outer periphery of said head and facing in a second axial direction opposite said first axial direction,
    a plurality of circumferentially spaced second cam faces disposed on said outer periphery and facing in said first axial direction,
said second valve section comprising:
    an end wall,
    a closure extending from said end wall in said second axial direction and disposed in said chamber, said closure including a passage-closing end facing said first passage for opening and closing said first passage in response to axial movement of said second section in first and second axial directions, respectively,
    a second fluid passage extending through said end wall and said closure and communicating with said chamber at a location spaced axially from said passage-closing end of said closure,
    a skirt extending from said end wall in said second axial direction and extending axially around said closure, said skirt spaced radially outwardly from said closure to form a space therebetween in which said head is disposed,
    a plurality of circumferentially spaced first cam follower faces disposed on said skirt, said first cam follower faces being engageable with respective first cam faces of said first section and being responsive to relative rotation between said first and second valve sections in a first rotary direction to produce movement of said first valve section in said second axial direction for closing said valve, and
    a plurality of circumferentially spaced second cam follower faces disposed on said skirt, said second cam follower faces being engageable with respective second cam faces of said first section and being responsive to said relative rotation in a second rotary direction opposite said first rotary direction to produce movement of said first section in said second axial direction for opening said valve.

2. A valve according to claim 1 wherein said chamber includes a cylindrical inner surface, and said closure includes a cylindrical outer surface, one of said cylindrical surfaces including an annular lip projecting radially into engagement with the other of said cylindrical surfaces to establish a friction fit between said first and second sections.

3. A valve according to claim 1 including a plurality of circumferentially spaced first and second cam elements projecting radially outwardly from an outer periphery of said head, said first and second cam elements forming said first and second cam faces, respectively.

4. A valve according to claim 3 including a plurality of circumferentially spaced first and second recesses formed in said skirt, said first and second recesses forming said first and second cam follower faces, respectively.

5. A valve according to claim 4 wherein said first and second recesses comprise apertures extending completely radially through said skirt.

6. A valve according to claim 4 wherein each of said first cam elements includes an inclined cam face facing in said first axial direction for engaging said skirt as said first and second valve sections are pushed axially together, for camming said skirt radially outwardly and enabling said first cam elements to enter said first recesses.

7. A valve according to claim 4 wherein said second recesses extend in said second axial direction all the way to an end of said skirt.

8. A valve according to claim 1 wherein said first valve section includes an axially projecting stem forming said first fluid passage, said stem having a length at least five times as great as a length of said head.

9. A valve according to claim 1 wherein one of said valve sections includes camming means for camming said skirt radially outwardly as said first and second valve sections are pushed axially together enabling said cam follower faces to engage said cam faces.

10. A valve comprising first and second plastic valve sections each being of one-piece molded construction, said first valve section comprising:
    an elongated hollow stem forming a first fluid passage which defines a longitudinal axis, an enlarged head disposed at one axial end of said stem and including a chamber which is coaxial with and communicates with said first passage, said chamber being open in a first axial direction,
    a plurality of circumferentially spaced first cam elements projecting radially outwardly from said head, each of said first cam elements including a cam face facing in a second axial direction, and
    a plurality of circumferentially spaced second cam elements projecting radially outwardly from said head, each of said second cam elements including a cam face facing in said first axial direction, said second valve section comprising:

an end wall, a closure extending from said end wall in said second axial direction and disposed in said chamber, said closure terminating in the form of a frusto-conical nose configured to engage said stem passage for opening and closing said valve in response to axial movement of said second valve section in said first and second axial directions, respectively, a second passage extending axially through both said end wall and said closure, said closure including a hole extending therethrough at a location spaced axially from said nose for communicating said second passage with said chamber, a cylindrical skirt extending from said end wall in said second axial direction and coaxially surrounding said closure, said skirt spaced radially from said closure to form a space therebetween in which said head is disposed, a plurality of first recesses formed in said skirt for receiving respective ones of said first cam elements, each of said first recesses including a cam follower face engageable with said cam face of its respective first cam element and being responsive to relative rotation between said first and second valve sections in one rotary direction to produce movement of said first valve section in said second axial direction for closing said valve, and a plurality of second recesses formed in said skirt for receiving respective ones of said second cam elements, each of said second recesses including a cam follower face engageable with said cam face of its respective second cam element and being responsive to said relative rotation in another rotary direction to produce movement of said first valve section in said first axial direction for opening said valve.

11. A valve according to claim 10 wherein one of said cylindrical surfaces of said chamber and said closure including an annular lip projecting radially against the other of said cylindrical surfaces to form a friction fit between said first and second valve sections.

12. A valve according to claim 11 wherein said first and second recesses comprise apertures extending completely radially through said skirt.

13. A valve according to claim 10 wherein each of said first cam elements includes an inclined cam face facing in said first axial direction for engaging said skirt as said first and second valve sections are pushed axially together, for camming said skirt radially outwardly and enabling said first cam elements to enter said first recesses.

14. A valve according to claim 10 wherein said second recesses extend in said second axial direction axially all the way to an end of said skirt.

* * * * *